(12) United States Patent
Anderson et al.

(10) Patent No.: US 7,878,202 B2
(45) Date of Patent: *__Feb. 1, 2011__

(54) SUCTION CATHETER ASSEMBLY

(75) Inventors: Stephen A. Anderson, Thompson Station, TN (US); Richard C. Dowdy, Colleyville, TX (US)

(73) Assignee: Egret Medical Products, Inc., Garland, TX (US)

( * ) Notice: Subject to any disclaimer, the term of this patent is extended or adjusted under 35 U.S.C. 154(b) by 719 days.

This patent is subject to a terminal disclaimer.

(21) Appl. No.: 11/438,931

(22) Filed: May 23, 2006

(65) Prior Publication Data

US 2006/0207605 A1 Sep. 21, 2006

Related U.S. Application Data

(63) Continuation of application No. 11/175,627, filed on Jul. 6, 2005, now Pat. No. 7,188,623.

(51) Int. Cl.
*A62B 9/02* (2006.01)
*A62B 9/06* (2006.01)
*A61M 1/00* (2006.01)

(52) U.S. Cl. .................................. 128/207.16; 604/118
(58) Field of Classification Search ......... 604/118–121; 128/220.26, 202.27, 204.18, 205.12, 205.24
See application file for complete search history.

(56) References Cited

U.S. PATENT DOCUMENTS

| | | | |
|---|---|---|---|
| 3,991,762 A | 11/1976 | Radford | |
| 4,569,344 A | 2/1986 | Palmer | |
| 4,836,199 A | 6/1989 | Palmer | |
| 4,850,350 A * | 7/1989 | Jackson | 128/207.16 |
| 4,872,579 A | 10/1989 | Palmer | |
| 5,073,164 A | 12/1991 | Hollister et al. | |
| 5,083,561 A * | 1/1992 | Russo | 128/207.16 |
| 5,088,486 A | 2/1992 | Jinotti | |
| 5,337,780 A | 8/1994 | Kee | |
| 5,354,267 A * | 10/1994 | Niermann et al. | 604/32 |
| 5,368,017 A | 11/1994 | Sorenson et al. | |
| 5,460,613 A * | 10/1995 | Ulrich et al. | 604/118 |
| 5,598,840 A | 2/1997 | Iund et al. | |
| 5,694,922 A | 12/1997 | Palmer | |
| 5,715,815 A | 2/1998 | Lorenzen et al. | |
| 5,730,123 A | 3/1998 | Lorenzen et al. | |
| 5,730,727 A * | 3/1998 | Russo | 604/118 |
| 5,735,271 A | 4/1998 | Lorenzen et al. | |
| 5,775,325 A | 7/1998 | Russo | |

(Continued)

Primary Examiner—Patricia M Bianco
Assistant Examiner—Kristen C Matter
(74) Attorney, Agent, or Firm—Gardere Wynne Sewell LLP

(57) ABSTRACT

A respiratory suction catheter assembly includes a manifold supporting a rotatable swivel member for engagement with an endotracheal tube, and a seal support body disposed on a boss of the manifold opposite the part supporting the swivel for supporting a catheter tube seal and a porous filter for filtering air flowing into and out of a flexible elongated sheath enclosing the catheter tube. The sheath includes opposed tapered ends secured to the seal support body and to a boss on a suction control valve housing. The valve housing supports a tapered plug closure member engageable with a resilient actuator and a slide-lock member. Certain components, including the sheath, the seal support body, the filter, the catheter tube seal and the catheter tube may be treated with an anti-microbial agent.

6 Claims, 6 Drawing Sheets

U.S. PATENT DOCUMENTS

| | | | |
|---|---|---|---|
| 5,779,687 A * | 7/1998 | Bell et al. ................... 604/265 |
| 5,919,174 A | 7/1999 | Hanson |
| 6,012,451 A | 1/2000 | Palmer |
| 6,070,582 A * | 6/2000 | Kee ....................... 128/207.16 |
| 6,109,259 A | 8/2000 | Fitzgerald |
| 6,142,980 A * | 11/2000 | Schalk ....................... 604/247 |
| 6,494,203 B1 * | 12/2002 | Palmer ................. 128/202.27 |
| 6,543,451 B1 | 4/2003 | Crump et al. |
| 6,575,944 B1 | 6/2003 | McNary et al. |
| 6,579,254 B1 | 6/2003 | McNary et al. |
| 6,588,425 B2 | 7/2003 | Rouns et al. |
| 6,615,835 B1 | 9/2003 | Cise et al. |
| 6,729,326 B1 | 5/2004 | Winterton et al. |
| 6,923,184 B1 * | 8/2005 | Russo ................... 128/207.14 |
| 6,935,339 B2 * | 8/2005 | Mattar et al. ........... 128/207.16 |

* cited by examiner

SUCTION CATHETER ASSEMBLY

CROSS REFERENCE TO RELATED APPLICATION

This application is a continuation of co-pending application Ser. No. 11/175,627 filed Jul. 6, 2005.

BACKGROUND OF THE INVENTION

Several developments have taken place with regard to providing suction catheter assemblies for use in obtaining lower respiratory tract secretions and in treating respiratory distress. However, continued improvements have been sought for suction catheter assemblies including providing a catheter assembly which will reduce the chance of causing respiratory infections, to reasonably assure that the catheter suction control valve is not inadvertently left in an open position, preventing cross-contamination to the care giver using the catheter assembly, minimizing twisting and manipulation problems associated with using the catheter assembly and related problems known to those skilled in the art. Still further, there has been a need to develop a respiratory suctioning device or suction catheter assembly intended to be used for longer periods of time than presently provided by the art, while enabling the user to maintain an open airway of the patient, improve oxygenation, remove accumulated tracheal and/or bronchial secretions, stimulate the cough reflex, prevent pulmonary aspiration of fluids and prevent infection and atelectasis. It is to these ends that the present invention has been developed.

SUMMARY OF THE INVENTION

The present invention provides an improved inline suction catheter assembly and, particularly, a catheter assembly intended for extended use, that is, for more than one week, for example.

In accordance with an important aspect of the invention certain components of the improved catheter assembly are treated using a non-leaching antimicrobial agent embodied in selected parts of the catheter assembly to reduce bacterial levels on the catheter tube and other components of the assembly. Such treated components may include (1) a flexible tapered sheath extending between a manifold and a control valve housing and enclosing the catheter tube, (2) the catheter tube, (3) a seal support body connected thereto, and (4) a catheter tube seal disposed in the seal support body.

Other important aspects of the invention include the provision of a suction control valve which requires a positive or deliberate actuation effort by the user to avoid accidental actuation, the control valve also being provided with a lock mechanism to enable the valve to be locked to prevent inadvertent or unwanted opening thereof.

The improved catheter assembly of the invention is also provided with a filter disposed on the seal support body of the catheter assembly and which is operable to vent the interior of the flexible sheath extending between the suction control valve and the seal support body, and to provide a pathway to allow exhausting of gases which might otherwise accumulate within the sheath or pass through the sheath toward the control valve or vice versa. The filter is treated with a suitable antimicrobial agent to minimize contamination to the user and the environment.

In accordance with a further aspect of the invention, the aforementioned sheath is tapered at opposite ends to facilitate handling and eliminate gathering or bunching of the sheath when the catheter is fully or substantially extended through the manifold.

Still further aspects of the present invention include the provision of an easily removable cap for connection to a so called T-body manifold or a cross type manifold, and a security string or tether comprising a monofilament suitably retained within the sheath to minimize tangling while serving the purpose of preventing the catheter from being withdrawn too far with respect to the manifold, for example. Yet further aspects of the invention include the provision of the seal support body to be rotatable with respect to the manifold and releasably connected to the manifold by a removable lock ring. The catheter tube may be of a configuration cooperable with structure, including a seal member, for example, to minimize or eliminate rotational twisting of the catheter tube with respect to the manifold whereby indicia disposed on the catheter tube may be easily viewable at all times. The seal support body is also provided with an advantageously configured auxiliary fluid injection port including a duckbill type check valve to facilitate insertion of auxiliary catheter devices and/or for lavaging or for cleaning the catheter tube.

The aforementioned advantages together with other important features and aspects of the invention, will be further appreciated by those skilled in the art upon reading the detailed description which follows in conjunction with the drawings.

DETAILED DESCRIPTION OF PREFERRED EMBODIMENTS

Figure 1:
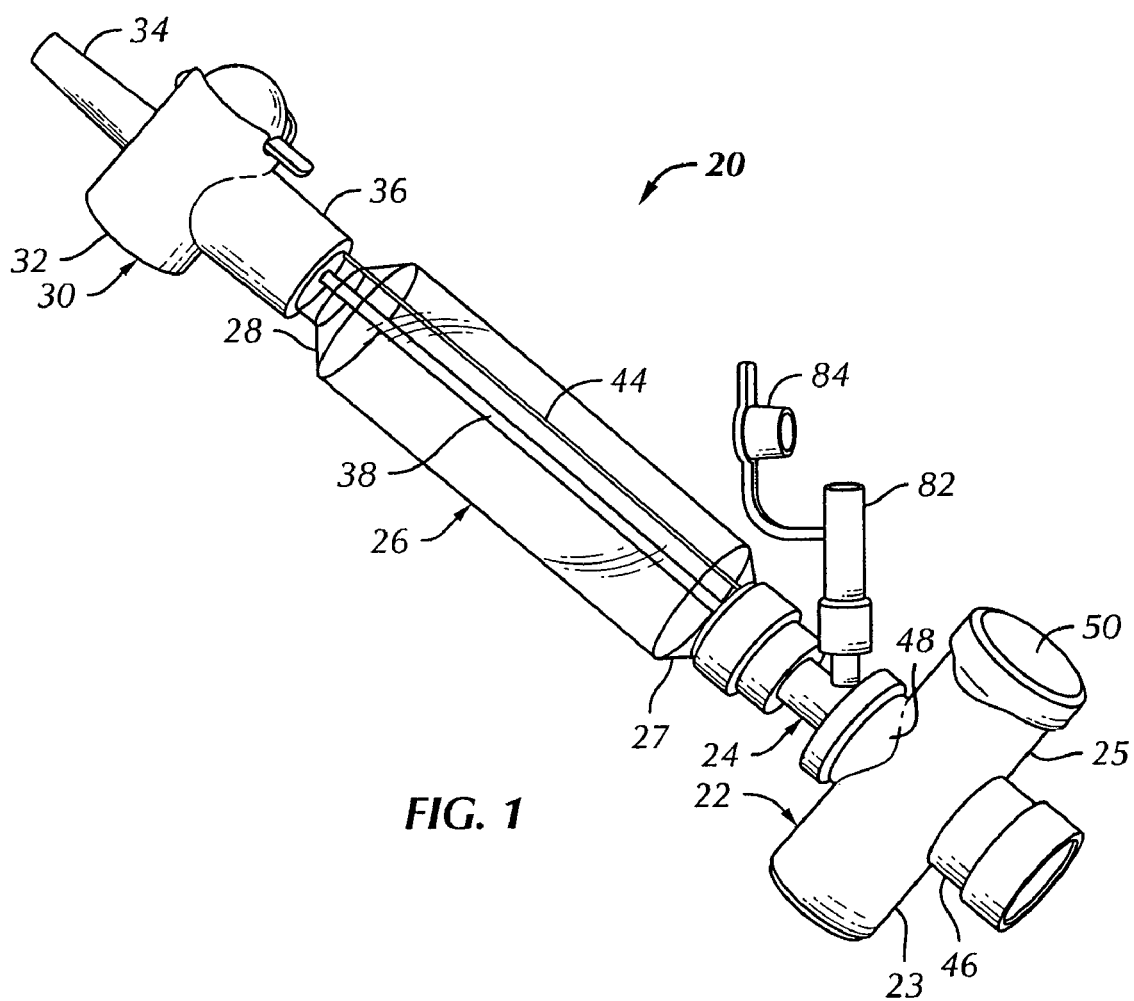
FIG. 1 is a perspective view of an improved suction catheter assembly of the present invention.

In the description which follows like parts are marked throughout the specification and drawing with the same reference numerals, respectively. The drawing figures are not necessarily to scale.

Referring to FIG. 1, there is illustrated a suction catheter assembly 20 in accordance with the invention. The catheter assembly 20 is characterized by a manifold member 22 operably connected to a seal support body 24 which is connected to an elongated, generally tubular, flexible, and preferably transparent sheath member 26. Sheath 26 is preferably tapered at opposite ends, thus being provided with opposed axially tapered end sections 27 and 28. Tapered section 27 is suitably connected to the seal support body 24 as will be further described herein. The opposite tapered section 28 is suitably connected to a suction control valve assembly 30. Suction control valve assembly 30 is characterized by a valve housing 32 which includes an axially extending tapered spigot part 34 adapted for connection to a vacuum conduit, not shown which, in turn, is adapted to be connected to a vacuum pump, also not shown. A sheath attachment sleeve 36 is connected to valve housing 32 in a manner to be further described herein for retaining the sheath 26 connected to the valve assembly 30.

Figure 2:
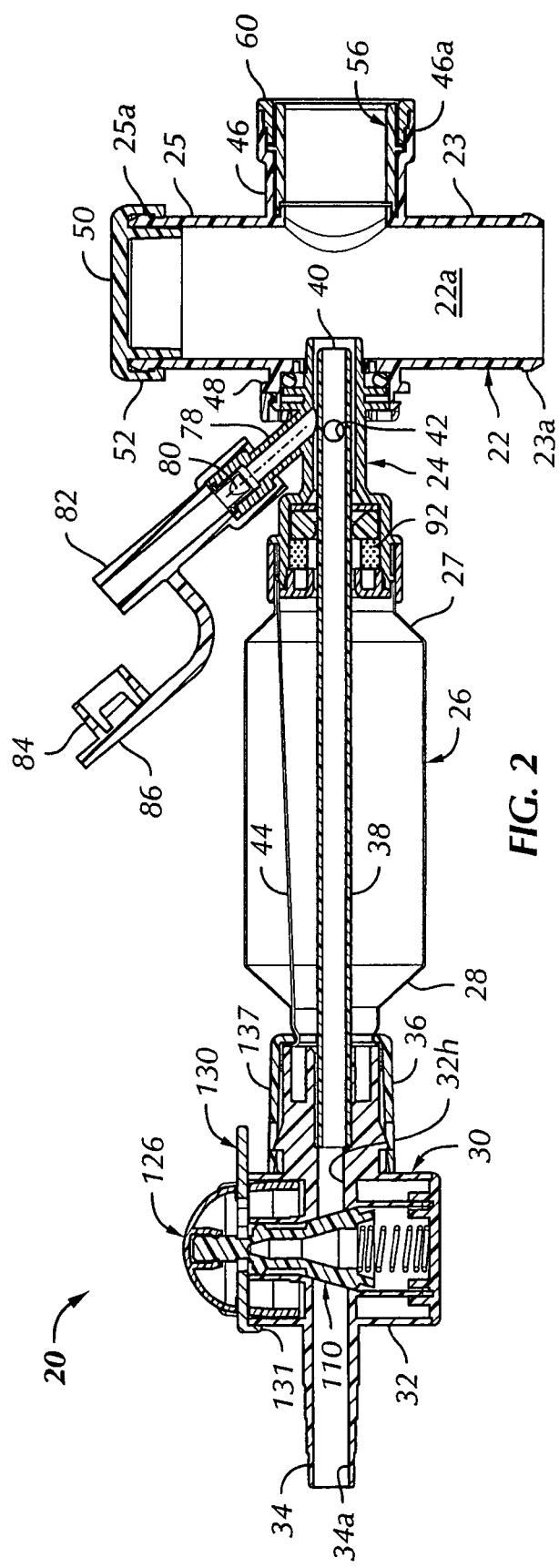
FIG. 2 is a longitudinal central section view of the catheter assembly.

Referring further to FIG. 2, the catheter assembly 20 includes an elongated flexible catheter tube 38, preferably formed of transparent polyvinyl chloride. Catheter tube 38 is connected to valve housing 32, extends longitudinally through the sheath 26 and into and through seal support body 24 and may be disposed in a typical stored position, as shown, wherein the catheter tube is essentially fully retracted. Catheter tube 38 includes a distal end 40 which is open for suctioning and conducting fluids therethrough in a known manner. Catheter tube 38 is also provided with one or more lateral ports 42, FIG. 2, formed therein and spaced a short distance from distal end 40. As further shown in FIG. 2, catheter assembly 20 includes an elongated flexible tether member 44 which extends between and is connected to the seal support body 24 and to the valve housing 32 in a manner to be described further herein. Tether 44 is disposed within the sheath 26 and is preferably characterized by a flexible monofilament "thread-like" member operable to limit the movement of the valve housing 32 away from the support body 24 to avoid retracting the catheter tube 38 too far into or even disconnected from the support body 24 in a direction to the left, viewing FIG. 2. Tether 44 also minimizes stretching of the relatively thin walled transparent, plastic sheath 26 beyond its elastic limit.

Referring further to FIG. 2, the manifold 22 is characterized by opposed tubular arms 23 and 25 which are coaxial and extend normal to an arm 46 which is also tubular and is co-axial with the seal support body 24 and the catheter tube 38. A tubular boss 48 is formed on manifold member 22 and is generally aligned with or coaxial with the tubular arm 46. Manifold 22 may be connected to a ventilator apparatus, not shown, in a conventional manner by a ventilator conduit connected to either the arm 23 or 25 or both, also in a known manner. If the passage of fluids through manifold member 22 is not required to be within both arms 23 and 25 a removable cap 50, as shown in FIG. 2, may be disposed on the arm 23 or 25 as shown. In this regard the distal ends of arms 23 and 25 are provided with shallow circumferential flanges 23a and 25a, respectively, which cooperate with a circumferential elastically deflectable flange 52 of cap 50 to allow snapping the cap or cover 50 onto or off of arm 23 or 25.

Figure 3:
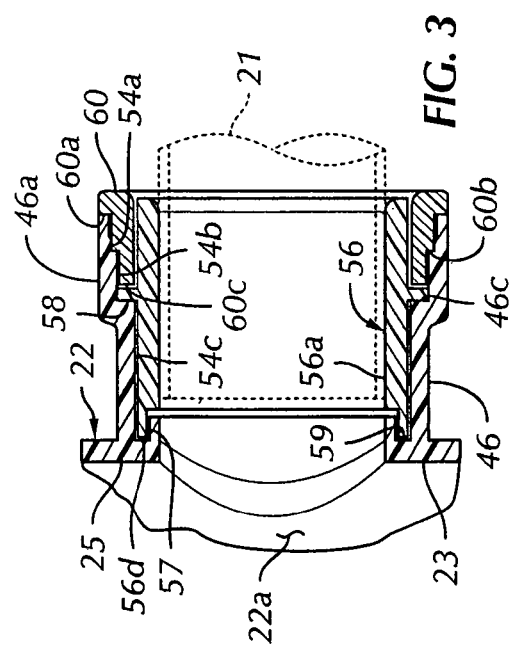
FIG. 3 is a detail section view on a larger scale showing the configuration of a swivel member supported in an arm of the manifold member of the catheter assembly shown in FIGS. 1 and 2.

Referring further to FIGS. 2 and 3, manifold tubular arm 46 is provided with an enlarged diameter distal end 46a and a stepped bore indicated by reference numerals 54a, 54b and 54c, FIG. 3. Stepped bore 54a, 54b, 54c is adapted to receive a tubular swivel member 56 which is operable to be connected to an endotracheal tube 21, FIG. 3, by sleeving the swivel member over a receiving end of such tube, as shown in FIG. 3. In this regard, a bore 56a of swivel member 56 may be tapered axially to provide for a wedge or force fit over the end of the aforementioned endotracheal tube. Swivel member 56 is provided with a circumferential radially outwardly extending flange 58 which is adapted to retain swivel member 56 within stepped bore 54a, 54b, 54c in cooperation with a tubular retainer member 60, FIG. 3, which is received in portions 54a and 54b of the aforementioned stepped bore. Retainer 60 is provided with spaced circumferential shoulders 60a and 60b engageable with cooperating shoulders formed on the enlarged diameter portion 46a of arm 46 to allow slight spacing between an end face 60c of retainer 60 and flange 58 of swivel member 56. Flange 58 is also engageable with a shoulder 46c formed in arm 46 by and between stepped bore portions 54b and 54c. Accordingly, an annular groove is formed between faces 60c and 46c to allow very limited axial movement of swivel member 56 in the stepped bore 54a, 54b, 54c of arm 46.

Referring further to FIG. 3, swivel member 56 is also provided with a counterbore portion 57 extending within an annular groove 59 formed at one end of stepped bore portion 54c, as illustrated, for receiving an annular end portion 56d of swivel member 56. Swivel member 56 is dimensioned to be retained in arm 46 by retainer 60 and to be rotatable in stepped bore 54a, 54b and 54c. The dimensional relationships between the arm 46 and the swivel member 56 are such that a tortuous leakage path is provided from interior chamber 22a of manifold 22, when the swivel member 56 is connected to an endotracheal tube, to substantially eliminate leakage of fluids between chamber 22 and the atmosphere. Accordingly, a somewhat labyrinth type seal is provided between swivel member 56 and arm 46 that would require fluids to flow in the clearance spaces between the swivel member 56, the groove 59, bore portions 54c, the space between shoulders or end faces 46c and 60c and the flange 58. Accordingly, such a leakage path is substantially tortuous and substantially eliminates flow of fluids between chamber 22a and atmosphere by way of the arm 46 and the swivel member 56.

Figure 6:
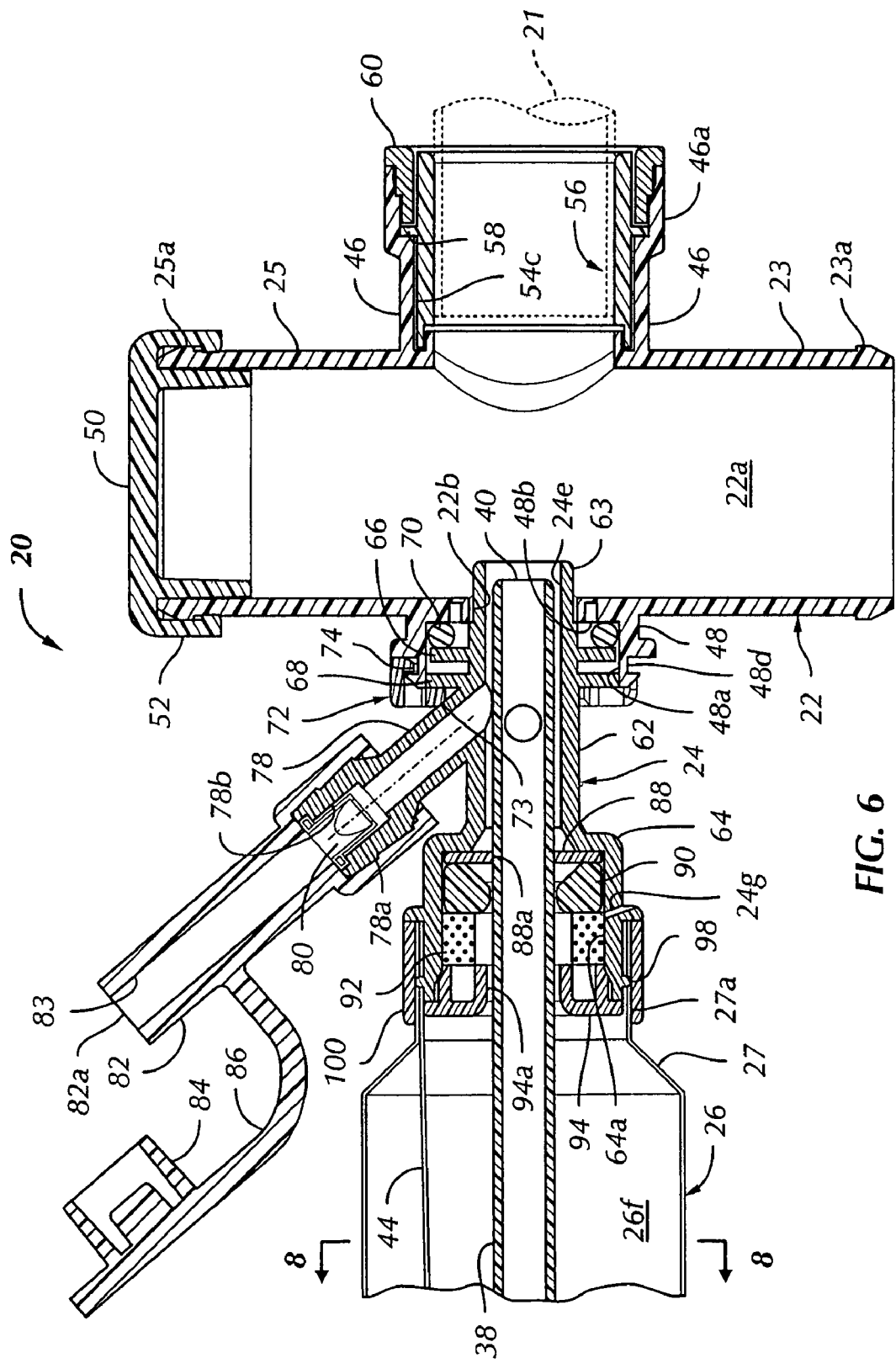
FIG. 6 is a section view on a larger scale of the manifold member and the seal support body.

Referring now to FIG. 6, the seal support body 24 comprises a generally elongated somewhat tubular member having a first tubular portion 62 coaxial with an enlarged diameter portion 64. Tubular portion 62 includes a distal end 63 which may project slightly into chamber 22a of manifold 22 when body 24 is assembled to the manifold member by registration with the tubular boss 48. In this regard, tubular boss 48 is provided with an axial bore 48a for receiving seal support body 24 and manifold 22 also includes a reduced diameter bore 22b coaxial with stepped bore 54a, 54b, 54c. Tubular portion 62 of body 24 includes closely spaced circumferential flanges 66 and 68 dimensioned to be received in close fitting relationship in bore 48a. Flange 66 is operable to retain an o-ring type seal 70 engaged therewith and with end face 48b of bore 48 to form a seal between body 24 and manifold 22. Seal support body 24 may be rotatable with respect to manifold 22 or suitably retained in engagement with tubular boss 48 and nonrotatably secured to the manifold 22. Seal support body 24 is retained connected to manifold 22 by a removable lock ring 72 which is engaged with boss 48 by registration with a circumferential groove 48d formed in boss 48.

Figure 7:
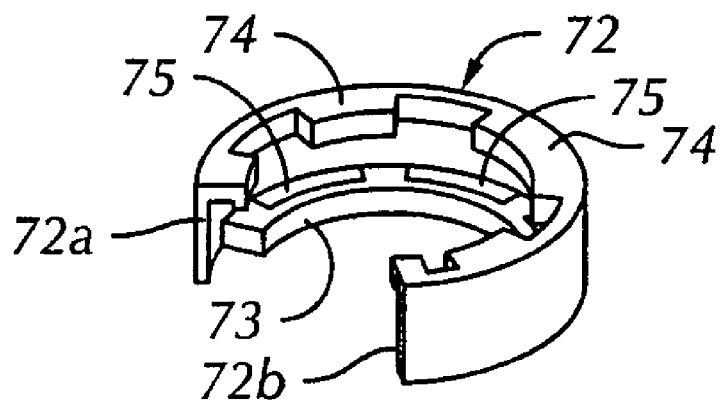
FIG. 7 is a perspective view of a removable lock ring for securing the seal support body to the manifold member.

Referring briefly to FIG. 7 also, lock ring 72 is characterized by a segment of a circle delimited by opposed ends 72a and 72b, a flange 73 and a segmented flange 74 as illustrated. Flange 73 is also provided with spaced apart slots 75 formed therein, as shown, to increase the flexibility of lock ring 72. Accordingly, lock ring 72 may be snapped onto tubular boss 48 with segmented flange 74 in registration with groove 48d while flange 73 retains seal support body 24 forcibly engaged with boss 48 within bore 48a and with at least some elastic deflection of o ring seal 70. In this way seal support body 24 may be easily releasably connected to manifold 22 and retained engaged with the manifold for rotation relative thereto, if desired.

Referring further to FIG. 6, seal support body 24 includes a branch conduit section 78 extending from the reduced diameter portion 62 at an acute angle of between about forty five degrees and sixty degrees and projecting away from manifold 22, as illustrated. Conduit section 78 forms a fluid injection port for catheter assembly 20 and is provided with an enlarged diameter distal end portion 78a and a stepped bore 78b in communication with central passage 24e formed in body 24. A suitable check valve, such as a so called duckbill type check valve 80, is disposed in stepped bore 78b and retained therein by a snap on tubular fitting 82, as illustrated in FIG. 6. Fitting 82 includes a central passage 83 formed therein and a tethered closure member 84 connected to the fitting by a flexible tether 86. Closure 84 may be snapped over the distal end 82a of fitting 82 to close off communication with passage 83. Fluids may be introduced through passage 83 and stepped bore 78b into passage 24e of seal support body 24 for purposes of cleaning catheter tube 38 and/or for introducing fluids into and through passage or chamber 22a for purposes known to those skilled in the art.

Referring still further to FIG. 6, enlarged diameter portion 64 of seal support body 24 includes a bore 64a coaxial with bore or passage 24e and operable to receive a circular disc seal member 88 having a central bore 88a formed therein and slightly smaller in diameter than the diameter of catheter tube 38. Seal member 88 is retained by a circular ring-like retainer member 90 in axially stacked relationship with a cylindrical tubular fluid filter member 92 also disposed in bore 64a. Seal 88, spacer or backing member 90 and filter 92 are retained in bore 64a by a suitable retainer cap 94 which may be press fitted in or adhesively bonded to enlarged diameter portion 64 of support body 24.

As further shown in FIG. 6, enlarged diameter portion 64 of seal support body 24 includes a circumferential radially outwardly projecting rib 98 formed thereon operable to receive a distal end portion 27a of sheath 26 as well as one end of tether 44 and retained tightly and sealingly engaged with body 24 by a tubular sleeve retainer member 100. Retainer 100 may be dimensioned to be a press fit over the rib 98 with the distal end 27a of sheath 26 sleeved over the rib and possibly including an end portion of tether 44 also forcibly engaged by sleeve 100 and rib 98. Retainer 94 includes a central bore 94a of greater diameter than the diameter of catheter tube 38 whereby air or other gases disposed within the interior chamber or space 26f of sheath 26 may be vented through filter 92 to atmosphere by way of one or more suitable ports 24g, one shown in FIG. 6, formed in enlarged diameter part 64 and opening into and through the bore wall forming the bore 64a. In this way air which is leaking past seal 88 will normally be vented through filter 92 and, as sheath 26 is collapsed during operation of the catheter assembly 20, air or other gases disposed within space or chamber 26f may also be vented through the filter. Also, as sheath 26 is extended and air is drawn back into the space 26f contamination of that space is substantially eliminated by providing filtration of air flowing through annular porous filter 92. Filter 92 may be formed of a suitable synthetic or resin foam material, such as polyethylene, and suitably treated with an antimicrobial agent of a type to be described further herein.

Figure 8:
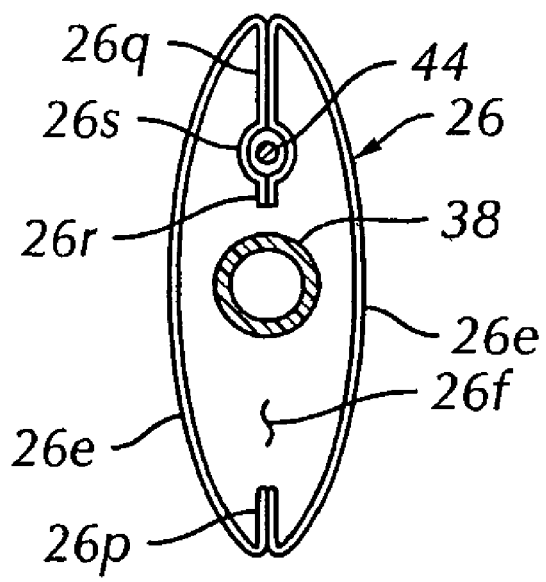
FIG. 8 is a transverse section view through the sheath of the catheter assembly taken along line 8-8 of FIG. 6 and illustrating one manner of supporting the tether extending between the control valve housing and the seal support body.

Referring briefly to FIG. 8, one preferred configuration of sheath 26 is where the sheath is formed of two opposed flexible sheets 26e formed of a polymer, such as polyurethane, having a wall thickness in the range of about 0.001 inches to 0.002 inches and heat sealed to each other at longitudinal seal points 26p, 26q and 26r to form the enclosed space 26f and to also form a channel 26s for disposition of the tether 44 loosely therein. Alternatively, the heat seal 26r may be eliminated and the tether 44 allowed to reside loosely in the larger space 26f.

Figure 4:
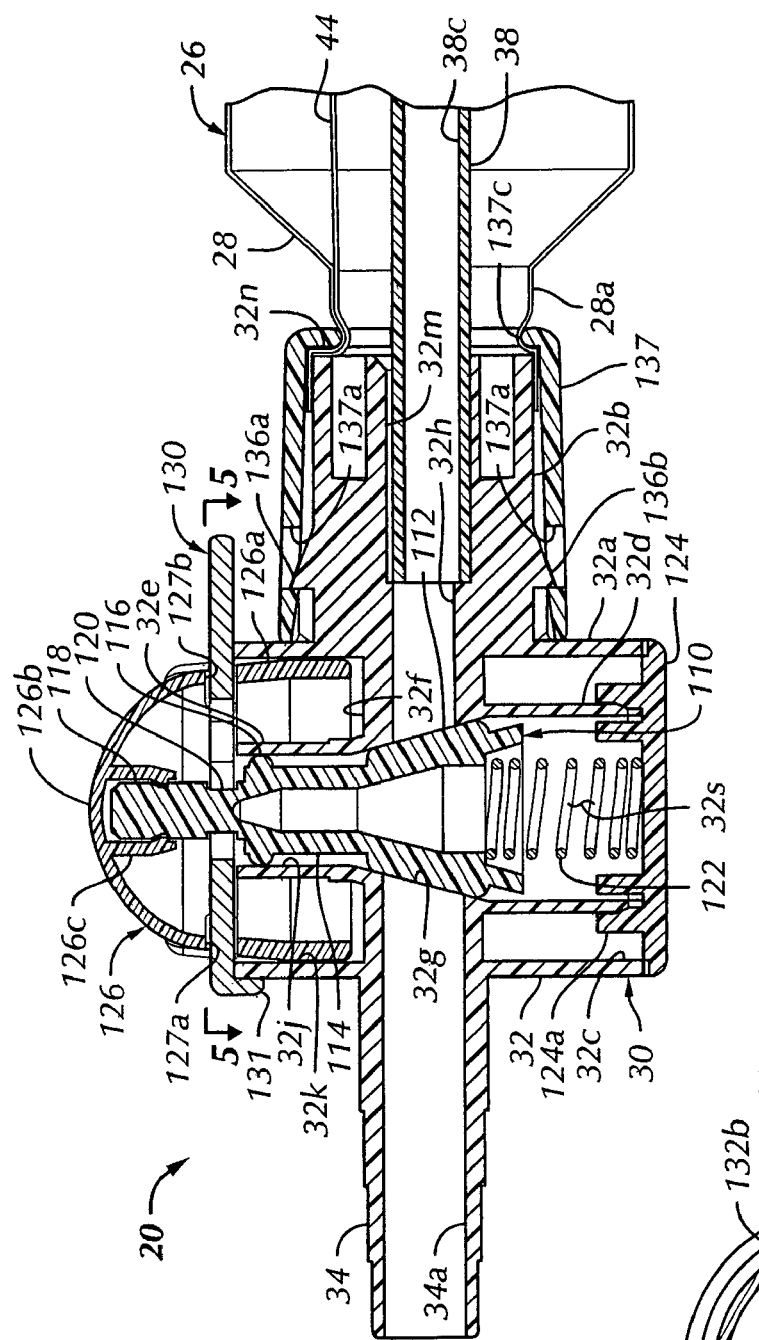
FIG. 4 is a detail section view on a larger scale of the suction control valve for the catheter assembly shown in FIGS. 1 and 2.

Referring now to FIGS. 2 and 4, and primarily FIG. 4, the suction control valve assembly 30 is shown in further detail. Valve housing 32 comprises a generally cylindrical body part 32a with a transverse generally cylindrical boss 32b projecting in a direction opposite the tubular conduit or spigot 34 and substantially coaxial therewith. Body part 32a includes a cylindrical outer wall 32c, a substantially coaxial tubular wall part 32d projecting in one direction and a reduced diameter tubular wall part 32e projecting in an opposite direction from a central transversely extending body part 32f. A tapered bore 32g is formed in body part 32f and opens to spaces formed by the tubular wall parts 32d and 32e for receiving a tapered plug valve closure member 110. Closure member 110 includes a tapered section 112 engageable with tapered bore 32g. Bore 32g intersects axially extending passageways 34a and 32h which are preferably coaxial. Closure member 110 includes an upwardly extending shaft portion 114, viewing FIG. 4, having a circumferential guide and seal member 116 integrally formed thereon and engageable with a bore wall 32j formed by tubular portion 32e. A reduced diameter head part 118 is also integrally formed on closure member 110. A circumferential groove 120 is interposed the head part 118 and the shaft portion 114 of closure member 110.

Valve closure member 110 is biased to a valve closed position by a coil spring 122 retained in valve body 32 by a removable cap 124 which may be snap fitted into engagement with tubular wall portions 32a and/or 32d or adhesively bonded to these members, if desired. Valve housing 32 includes a cylindrical bore 32k formed substantially coaxial with and by wall 32c for receiving a resilient somewhat cup shaped valve actuator member 126. Actuator member 126 has a cylindrical skirt portion 126a integrally joined to a generally hemispherical actuator button portion 126b. Actuator 126 may be formed of a suitable resilient material, such as polypropylene, and having an elastic memory biasing the actuator to the position shown, but allowing the button portion 126b to be axially deflected to engage valve closure member 110 and move the closure member downwardly, viewing FIG. 4, to open valve 30 to allow fluids to flow primarily from catheter tube 38 through passage 32h tapered bore 32g and passage 34a. An annular projection 126c is integrally formed on actuator 126 and snuggly engages head portion 118 of closure member 110 to assist in biasing the closure member to a valve closed position, thanks to the elastic memory of actuator 126. Of course, coil spring 122 also urges the closure member 110 toward the valve closed position and also to restore the actuator member 126 to the position shown in FIG. 4.

Figure 5:
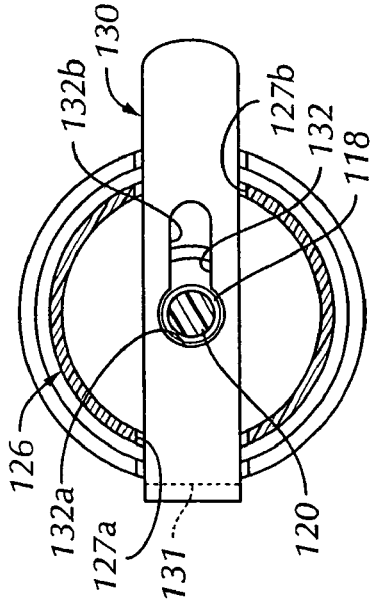
FIG. 5 is a section view showing the valve lock member and taken along line 5-5 of FIG. 4.

Actuator member 126 includes opposed transverse slots 127a and 127b, see FIG. 5 also, for receiving an elongated flat plate shaped lock member 130 therein, respectively. Lock member 130 includes a depending tab 131 at one end thereof and a somewhat keyhole shaped slot 132 formed therein, the enlarged diameter portion of which is designated by the numeral 132a and is of a slightly larger diameter than the diameter of the closure member head portion 118 so that the lock member may be sleeved over the head portion and allowed to register with the circumferential groove 120. In this way, when the lock member 130 is moved from the position shown in FIGS. 4 and 5, to the left, viewing FIGS. 4 and 5, the keyhole slot part 132b registers in groove 120. Slot 132b is of a width smaller than the diameter of head portion 118 and, thus, will not permit the valve closure member 110 to move to the valve open position. Accordingly, the lock member 130 is provided to be conveniently slidable from the position shown in FIG. 4, allowing the closure member 110 to open, to a position toward the left, viewing FIG. 4, to prevent the valve closure member from moving to an open position.

Referring still further to FIG. 4, the valve body part or boss 32b includes opposed retainer teeth 136a and 136b formed thereon and engageable with a cylindrical sleeve member 137 which is adapted to be sleeved over the boss 32b and provided with opposed slots 137a for registration with the teeth 136a and 136b to lock the retaining sleeve 137 in engagement with the valve housing 32. An enlarged bore or passage part 32m in boss 32b receives an end of catheter tube 38, as shown, and whereby catheter tube 38 may be suitably secured in bore 32m by an adhesive or chemical or thermal bonding with valve housing 32. Retaining sleeve 137 is adapted to be sleeved over the distal end 28a of sheath 26, as shown, and is provided with a suitable cylindrical opening 137c for receiving the sheath distal end whereby the sheath distal end may be trapped between an end face 32n of boss 32b and the sleeve 137. Tether 44 may also be trapped in the same manner. Retaining sleeve 137 and boss 32b are thus configured to allow easy assembly of the valve body 32 to the sheath 26 while snuggly retaining the sheath engaged with the valve 30.

The valve 30 substantially eliminates leakage of contaminated fluids to the exterior of the valve. A substantial seal is provided between the annular ridge or rim 116 and bore wall 32j to prevent leakage from tapered bore 32g into the interior space delimited by the actuator 126. At the opposite end of bore 32g, the cap 124 is provided with a cylindrical flange 124a operable to be in fluid tight engagement with wall 32d to prevent leakage from space 32s, FIG. 4.

The tapering of the sheath 26 at its opposite ends 27 and 28 is advantageous to minimize unwanted gathering of the sheath when the valve 30 is moved toward the seal support body 24 to extend the catheter tube 38 through the bore of swivel member 56 and into the patient via an endotracheal tube. The antimicrobial treated filter 92 minimizes leakage of contaminated fluids from within the interior of the sheath 26 to atmosphere or vice versa. Hermetic sealing of the opposite ends of the sheath to the seal support body 24 and to the valve 30 is obtained without the use of chemical adhesives. The seal support body 24 advantageously allows rotation of the manifold 22 relative to the remainder of the catheter assembly 20. The catheter tube 38 may be provided with suitable key means comprising one or more longitudinal projections or, alternatively, longitudinal keyways or grooves, not shown, extending along the catheter tube and cooperating with means, not shown, on body 24, for example, to prevent rotation of the catheter tube relative to the body 24. Accordingly, suitable indicia as described hereinbelow, may be disposed on the catheter tube 38 and which may be viewed by a person, looking generally downward on the catheter assembly 20, as it is being used, to determine the extension of the tube into a patient. The provision and position of inclination of the branch conduit or port 78 is adapted to facilitate lavaging a patient and cleaning of the catheter tube 38. The check valve 80 is adapted to facilitate lavaging and cleaning of the catheter tip and to prevent cross-contamination.

Figure 9:
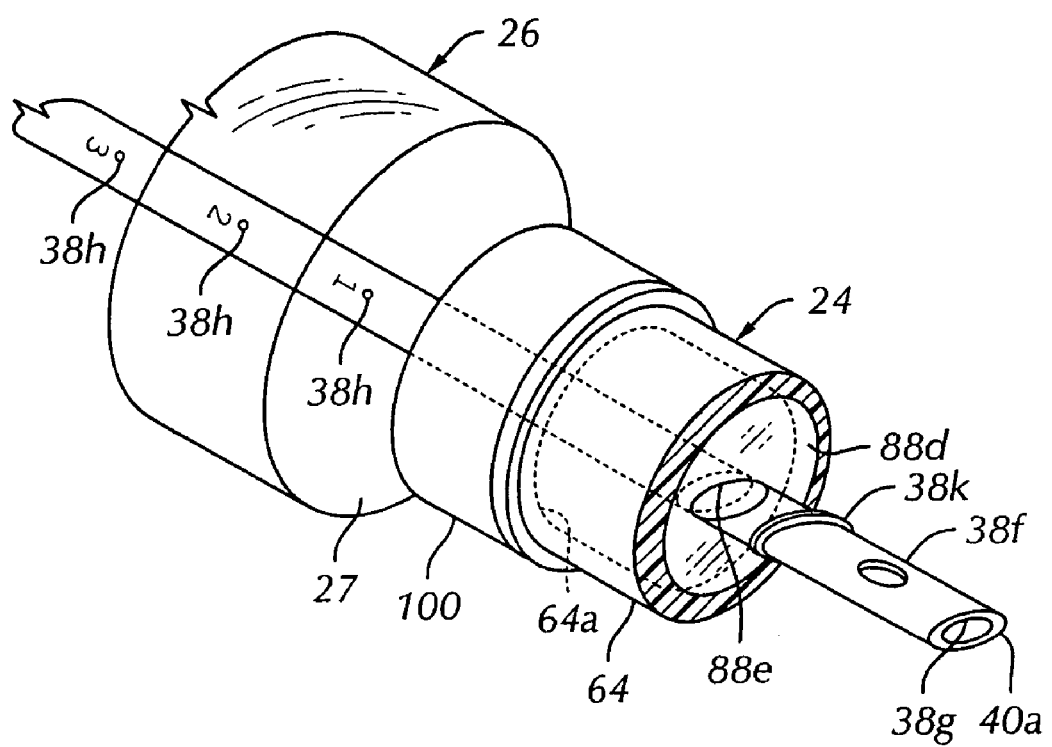
FIG. 9 is a detail perspective view showing a modified catheter tube supported in a way to minimize rotational twisting.

Referring briefly to FIG. 9, one preferred embodiment of a catheter tube which is essentially non-rotatable with respect to the body 24 is illustrated and generally designated by the numeral 38f. Catheter tube 38f has an internal passage or lumen 38g opening to a distal end 40a and has a cross-sectional shape which is non-circular, preferably elliptical. Catheter tube 38f projects through a modified seal 88d disposed in and non-rotatable with respect to enlarged diameter portion 64 of seal support body 24. Seal 88d includes an elliptical bore 88e dimensioned to be in tight fitting but slidable relationship with respect to catheter tube 38f. Catheter tube 38f may be elliptical in cross sectional shape throughout its entire length or only that portion of its length which is likely to be engaged with seal 88d.

As also shown in FIG. 9, catheter tube 38f is provided with suitable indicia 38h on an upward facing side of the elliptical cross sectional shape of the tube for use by an operator of the catheter tube assembly to judge how far the catheter tube is being inserted into a patient's respiratory tract. Tube 38f may include suitable stop means, such as an annular projection or collar 38k, integrally formed thereon, to limit withdrawal of the tube by engagement with seal 88d. Accordingly, a modified catheter assembly employing the tube 38f and seal 88d enjoys all of the benefits of the invention previously described while providing the added benefits of minimizing rotation or twisting of the catheter tube during use. Still further, the projection 38k prevents excessive withdrawal of the tube which might result in disengagement from the tube seal and excessive stretching of the sheath and tether members. The configuration of catheter tubes 38 and 38f and the support structure therefor, including the rotatable seal support body 24, provides a more user friendly and longer lived catheter assembly.

Certain parts of the catheter assembly 20 are advantageously treated with a permanent antimicrobial agent intended to reduce bioburden and the chance of respiratory infections. For example, the seal support body 24 may be treated with an antimicrobial agent by coating such agent thereon or impregnating such agent in the resin of the material forming the body 24 when the body is formed.

The manifold 22, the body 24 and the components of valve 30, except for the spring 122, are all preferably formed of injection molded acrylic, for example. The acrylic resin may be mixed with the antimicrobial agent prior to molding or otherwise fabricating the catheter parts. The same procedure may be utilized in fabricating the sheath 26 and the catheter tubes 38 and 38f. One suitable antimicrobial agent is available from BIOSAFE division of Aegis, Pittsburgh, Pa., under the product designation AEM 5700. One procedure for obtaining parts such as the body 24, the seals 88 and 88d, the filter 92, the sheath 26 and the catheter tubes 38 and 38f is to coat the resin particles used to form these parts with the above-mentioned antimicrobial agent prior to introducing the particles into an extrusion process, which may or may not include heating the particles, to form a flowable mass that may be extruded or used to injection mold certain ones of the parts. Alternatively, pre-formed parts may be coated with the antimicrobial agent. The catheter tubes 38 and 38f may be fabricated to include the anti-microbial agent using either one of the processes described above.

One important aspect of the AEM 5700 anti-microbial agent that is advantageous in connection with the present invention is the non-leaching character of this agent. Once the antimicrobial agent has come into contact with a surface, chemical changes occur which prevent it from being subsequently removed. Therefore, the antimicrobial material remains on the substrate to which it has become attached and does not enter the environment. Treatment of the surfaces of the aforementioned parts of the catheter assembly 20 may be carried out by applying the antimicrobial agent in a water solution and upon removal of the water the non volatile silane ingredient of the agent forms covalent bonds with the surface of the material of which the aforementioned parts are formed.

A major advantage of the catheter assembly 20 is the length of time the assembly may be used in treating a patient. Ventilator associated pneumonia (VAP) is a major health issue that must be dealt with for patients which require ventilation greater than about 48 hours. Accordingly, by use of a device in accordance with the invention, it is indicated that some reduction in the onset of VAP may be expected. Moreover, the costs for treatment of VAP can be extremely expensive for a hospital facility, not to mention life-threatening for the patient. By utilizing equipment, such as the catheter assembly 20, which may control the germination of bacteria in an advantageous manner these concerns may be eliminated or substantially reduced.

Although a preferred embodiment of the invention has been described in detail, those skilled in the art will recognize that various substitutions and modifications may be made without departing from the scope and spirit of the appended claims.

What is claimed is:

1. A suction catheter assembly for connection to an endotracheal tube for treating a patient comprising:
a suction control valve assembly; an elongated catheter tube connected at one end to said suction control valve assembly; a manifold including a first arm including a fitting for connection to said endotracheal tube and a second arm for connection to a ventilating device and a tubular boss having a circumferential groove formed therein and substantially aligned with said first arm and including a bore receiving one end of a seal support body releasably and rotatably connected to said manifold at said tubular boss, said seal support body connected to said manifold and including a catheter tube seal supported thereby, wherein said seal support body is connected to said manifold at said tubular boss by a removable lock ring having a segmented flange, said segmented flange being in registration with said tubular boss circumferential groove; and an elongated flexible sheath interconnecting said suction control valve assembly and said seal support body and forming an enclosed space for extension of said catheter tube therethrough, said sheath being flexible and collapsible for extending said suction control valve assembly toward said manifold to insert said catheter tube through said endotracheal tube, said sheath including opposed portions at opposite ends for connection with said seal support body and with a second boss formed on a valve housing of said suction control valve assembly, and said sheath being formed of polyurethane, wherein said catheter tube is one of coated and impregnated with an antimicrobial agent.

2. The suction catheter assembly of claim 1, wherein:
at least one of said manifold, catheter tube seal, and sheath is also coated and impregnated with an antimicrobial agent.

3. The suction catheter assembly of claim 1 or 2, wherein:
said valve housing of said suction control valve includes a spigot for connection to a source of vacuum and said second boss, said second boss extending in a direction opposite said spigot, passage means in said second boss and in said spigot forming a flow path for fluids passing into said valve housing from said catheter tube, a tapered bore intersecting said passage means and a tapered plug closure member disposed in said tapered bore and engageable with a bore wall of said tapered bore intersecting said passage means in said spigot and said second boss, respectively.

4. The catheter assembly set forth in claim 3 including:
an axial stem of said closure member engageable with a resilient valve actuator member supported on said valve housing, said valve actuator member having an elastic memory operable to provide for deflection of said valve actuator member to move said valve closure member toward a valve open position and to exert a biasing force urging said valve closure member toward a valve closed position.

5. The catheter assembly set forth in claim 4 wherein:
said valve actuator member comprises a skirt disposed in a bore formed in said valve housing and a hemispherical portion operable to be engaged by an operator of said catheter assembly for deflection to move said closure member toward an open position.

6. The catheter assembly set forth in claim 4 or 5 including:
spring means biasing said closure member in a valve closed position and disposed in said valve housing.

* * * * *